(12) United States Patent
Bryce-Smith

(10) Patent No.: US 6,288,115 B1
(45) Date of Patent: *Sep. 11, 2001

(54) USE OF ZINC SALTS OF CONJUGATED LINOLEIC ACIDS TO TREAT SKIN DISORDERS

(75) Inventor: Derek Bryce-Smith, Reading (GB)

(73) Assignee: Kappa Pharmaceuticals Limited, Reading (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,305

(22) Filed: May 9, 2000

Related U.S. Application Data

(63) Continuation of application No. 09/284,047, filed as application No. PCT/GB97/02854 on Oct. 16, 1997.

(30) Foreign Application Priority Data

Oct. 17, 1996 (GB) .................................................. 9621630

(51) Int. Cl.[7] .................................................. A61K 31/20
(52) U.S. Cl. .............................................................. 514/560
(58) Field of Search ..................................... 514/560, 494

(56) References Cited

U.S. PATENT DOCUMENTS 5,792,449 * 8/1998 Bryce-Smith ..................... 424/78.02

FOREIGN PATENT DOCUMENTS

WO-95/13806-A1 * 5/1995 (WO) .

OTHER PUBLICATIONS

Belury, M., "Conjugated dienoic linoleate: a polyunsaturated . . . ", abstract, Nutrition Reviews, Apr. 1995, vol. 53, pp. 83–89.*
Parodi, P. "Milk fat components: possible chemopreventive agents for cancer . . . " abstract, Austrian Juournal of Dairy Technology, 1996, vol. 51(1), pp. 24–32.*
Belury et al., "Dietary conjugated linoleic acid modulation of phorbol . . . ", abstract, Nutr. Cancer, 1996, vol.26(2), pp. 149–157.*
Parodi, P., "Conjugated linoleic acid: An anticarcinogenic fatty acid . . . " abstract, Austrain Journal of Dairy technology, 1994, vol. 49(2), pp. 93–97.*

* cited by examiner

Primary Examiner—William R. Jarvis
Assistant Examiner—Vickie Kim
(74) Attorney, Agent, or Firm—Renner, Otto, Boisselle & Sklar

(57) ABSTRACT

The invention is related to a pharmaceutical composition for use in treating skin disorders comprising substantially the zinc salt of at least one conjugated linoleic acid, wherein the composition is comprising at least 50% the zinc salt of at least one conjugated linoleic acid.

3 Claims, No Drawings

USE OF ZINC SALTS OF CONJUGATED LINOLEIC ACIDS TO TREAT SKIN DISORDERS

This application is a continuation of application Ser. No. 09/284,047 filed on Oct. 16, 1997 which is a 371 of PCT/GB97/02854 Oct. 16, 1997.

The present invention concerns compositions and their use in the treament of skin disorders particularly, but not limited, to eczema, psoriasis and dermatitis, and also compositions and their use in treatment of cancer, particularly skin cancer.

Conjugated linoleic acid and linoleic acid are well-known for their therapeutic, particularly chemotherapeutic, properties (see, for example, Belury, M. A., 1995 Nutrition Reviews,53 (4): 83–39 and references therein; Pariza, M. W., Chemistry & Industry, Jun. 16, 1997, 464–466; EP 0 087 863; EP 0 044 341; EP 0 078 434; EP 0 003 407; EP 0 057 175; EP 0 071 357; EP 0 085 579; EP 0 139 480), and have comprised non-essential components of compositions for treating skin disorders (EP 0 727 991). WO 95/13806 discloses the use of a composition comprising zinc salts of 68% (unconjugated) linoleic acid and 10% conjugated isomers of linoleic acid for use in treating skin disorders.

However, the present inventor has now found that zinc salts of conjugated linoleic acids have an unexpectedly great efficacy in the treatment of skin disorders when compared to for example unconjugated zinc linoleate.

According to the present invention, there is provided a composition for use in treating skin disorders comprising substantially the zinc salt of at least one conjugated linoleic acid. The composition may be used in a method of treating skin disorders.

Also provided is the use of a composition comprising substantially the zinc salt of at least one conjugated linoleic acid in the manufacture of a medicament for treating skin disorders.

Also provided is a method of manufacture of a medicament for treating skin disorders comprising the use of a composition comprising substantially the zinc salt of at least one conjugated linoleic acid.

Also provided is a method of treatment of a skin disorder comprising the use of a composition comprising substantially the zinc salt of at least one conjugated linoleic acid.

Methods of manufacture and use of the compositions and medicaments of the present invention will be readily apparent to one skilled in the art and are exemplified in the Examples below.

The composition may comprise at least 50%, for example at least 60%. 70%, 80% or 90%, the zinc salt of at least one conjugated linoleic acid. For example it may substantially comprise the zinc salt of a conjugated linoleic acid or it may comprise a substantially greater proportion of the zinc salt or salts of at least one conjugated linoleic acid than of zinc linoleate The present inventor has found that the zinc salts of conjugated linoleic acids have a surprisingly great efficacy, compared to that of conjugated linoleic acids alone (which may act as irritants) and of zinc linoleate, when used in the treatment and/or prophylaxis of skin disorders such as eczema, psoriasis, cold sores (herpes) and dermatitis.

The conjugated linoleic acids are a large family of molecules. Dienoic conjugated linoleic acids may be used as the basis of the zinc salts of the present invention. For example, 9,11-octadecadienoic acid or 10,12-octadecadienoic acid may be used. These unsaturated molecules contain double bonds and so there are a number of geometric isomers of the molecules, for example cis9tans11-octadecadienoic acid and trans9cis11-octadecadienioc acid.

The compositions of the present invention may be used in conjunction with a pharmaceutically acceptable carrier, diluent or excipient. Such carriers, diluents and excipients are well known—see for example Remington s Pharmaceutical Sciences and US Pharmacopeia (1984) Mack Publishing Company, Easton, Pa.

The composition may also comprise at least one antioxidant, for example tocopherol (Vitamin E).

The composition may also comprise for example zinc linoleate and/or the zinc salt of at least one other fatty acid. Conjugated lioleic acids are usually prepared by the isomerization of linoleic acid, and are therefore liable to contain various residues of linoleic acid. Thus zinc linoleate may be among the zinc salts formed when the isomerised linoleic acid is converted into zinc salts.

The zinc salts of conjugated linoleic acids appear to be more effective than zinc salts of other fatty acids, and (see examples B and C below) do not owe their activity to the presence of zinc alone.

Medicaments and compositions according to the present invention may be administered in doses (i.e. concentrations and quantities) sufficient to effect the desired prophylactic or therapeutic result. Such doses may be readily determined using simple dose-response experiments.

The doses may be such that they are substantially non-irritant to the patient

According to a further aspect of the present invention, there is provided a composition for use in treating cancer comprising substantially the zinc salt of at least one conjugated linoleic acid. The composition may be used in a method of treating cancer.

Also provided is the use of a composition comprising substantially the zinc salt of at least one conjugated linoleic acid in the manufacture of a medicament for treating cancer.

Also provided is a method of manufacture of a medicament for treating cancer comprising the use of a composition comprising substantially the zinc salt of at least one conjugated linoleic acid.

Also provided is a method of treatment of a cancer comprising the use of a composition comprising substantially the zinc salt of at least one conjugated linoleic acid.

Methods of manufacture and use of the compositions and medicaments of the present invention will be readily apparent to one skilled in the art, particularly with reference to the Examples below.

The composition may comprise at least 50% for example at least 60%. 70%, 80% or 90%, the zinc salt of at least one conjugated linoleic acid. For example it may substantially comprise the zinc salt of a conjugated linoleic acid or it may comprise a substantially greater proportion of the zinc salt or salts of at least one conjugated linoleic acid than of zinc linoleate.

A zinc salt may for example be of 9,11-octadecadienoic acid or 10,12-octadecadienoic acid.

The zinc salts of the compositions of the present invention for the treatment and/or prophylaxis of skin disorders also appear to be useful in the treatment and/or prophylaxis of cancer, particularly epidermal cancers such as skin cancer.

The medicament may additionally comprising a pharmaceutically acceptable carrier, diluent or excipient.

The invention will be further apparent from the following description and examples which show, by way of example only, zinc salts of conjugated linoleic acids for use in the treatment of skin disorders.

Example A

Preparation of zinc conjugated linoleates (ZCL) in a formulation suitable for topical application 215 g of Pamolyn (RIM)380 (Hercules Inc., Hercules Plaza, Wellington, Del. 19894USA) containing ca. 69% of conjugated linoleic acids was heated to 70° C. with 500 g Emulsifying Ointment BP: 32.5 g of zinc oxide was added slowly with stirring. Heating was continued for a further 5 minutes, then 1,250 ml of boiling demineralised water was slowly added with stirring. The whole hot product was then emulsified by vigorous mechanical agitation and allowed to cool, giving a white semi-cream which when cool was well absorbed on topical application to the skin with gentle rubbing.

The physical characteristics of the product were varied by increasing or decreasing the proportion of water during the preparation. One half of the above proportion of water gave an ointment, whereas increasing the proportion of water by 50% gave a cream.

Example B

A male patient suffering from eczema, mainly on the arms, was treated by daily topical application of the ZCL semi-cream of Example A. The condition was completely cured within 4 days.

Example C

Previous treatment as in Example B with a product similar to that of Example A but containing only one-seventh of the proportion of ZCL, but the same proportion of zinc, had improved the eczema to a limited extent but had not provided a complete cure even after application over 2 weeks.

Example D

The product prepared as in Example A was used to treat a female patient suffering from facial psoriasis. This condition was greatly improved within 1 day and essentially cured within 2 days.

Example E

A male patient aged 70 years suffering from pruritus of the legs and scalp was treated by topical application of a semi-cream prepared as in Example A. Inching ceased within 10–15 minutes.

Example F

A male patient aged 55 years experienced severe sunburn. A single application of the semi-cream of Example A rapidly removed all soreness and discomfort.

Example G

A female patient of 55 years age suffered severe discomfort caused by pressure sores on the trunk. A single application of the semi-cream of Example A rapidly alleviated all soreness and discomfort

Example H

A male patient of 55 years age suffered from an erupted (i.e. broken skin) cold sore (Herpes). Treatment with the semi-cream of Example A rapidly removed the soreness and discomfort, and the condition was essentially cured within 2 days.

Example I

A male patient suffering from skin cancer applied the semi-cream of Example A on a daily basis to an area of skin cancer. Over a period of four months, the appearance of the affected area improved (although the cancer did not totally disappear) and itching of the affected area stopped. Discontinuation of treatment resulted in the recurrence of itching at the affected area.

Example J

A female patient had a patch of discolored skin on one ankle which was medically diagnosed as skin cancer. Application to the affected area of the semi-cream of Example A completely stopped unpleasant itching felt at the affected area. Continued use over a period of about six months resulted in the patch of cancerous skin becoming much less raw in appearance and it started to break up into islets separated by skin of more normal appearance.

What is claimed is:

1. A composition for use in treating skin disorders selected from any one of the group of eczema, psoriasis, cold sores and dermatitis, comprising at least 50% of the zinc salt of at least one conjugated linoleic acid.

2. A composition according to claim 1, the composition comprising at least 60% of the zinc salt of at least one conjugated linoleic acid.

3. A composition according to claim 1 wherein the conjugated linoleic acid is selected from the group of 9,11-octadecandienoic acid and 10,12-octadecadienoic acid.

* * * * *